(12) United States Patent
Chornenky et al.

(10) Patent No.: US 11,642,545 B2
(45) Date of Patent: May 9, 2023

(54) METHOD AND APPARATUS FOR TREATMENT OF DIABETIC RETINOPATHY (DR)

(71) Applicant: Minnesota Medical Physics LLC, Eden Prairie, MN (US)

(72) Inventors: Victor I. Chornenky, Minnetonka, MN (US); Ali Jaafar, Eden Prairie, MN (US)

(73) Assignee: Minnesota Medical Physics LLC, Eden Prairie, MN (US)

( * ) Notice: Subject to any disclaimer, the term of this patent is extended or adjusted under 35 U.S.C. 154(b) by 1058 days.

(21) Appl. No.: 16/366,551

(22) Filed: Mar. 27, 2019

(65) Prior Publication Data

US 2019/0299020 A1   Oct. 3, 2019

Related U.S. Application Data

(60) Provisional application No. 62/761,542, filed on Mar. 29, 2018.

(51) Int. Cl.

| | |
|---|---|
| *A61N 2/02* | (2006.01) |
| *A61N 2/00* | (2006.01) |
| A61N 1/40 | (2006.01) |
| A61N 1/36 | (2006.01) |
| A61K 31/00 | (2006.01) |

(Continued)

(52) U.S. Cl.
CPC .............. *A61N 2/02* (2013.01); *A61N 2/006* (2013.01); *A61B 2018/00321* (2013.01); *A61K 31/00* (2013.01); *A61N 1/326* (2013.01); *A61N 1/3606* (2013.01); *A61N 1/36046* (2013.01); *A61N 1/40* (2013.01)

(58) Field of Classification Search
CPC . A61N 2/00; A61N 2/02; A61N 2/004; A61N 2/006
See application file for complete search history.

(56) References Cited

U.S. PATENT DOCUMENTS

| | | | |
|---|---|---|---|
| 6,406,419 B1 * | 6/2002 | Farahmand | A61N 2/06 351/158 |
| 9,486,638 B2 | 11/2016 | Chornenky et al. | |

(Continued)

*Primary Examiner* — John P Lacyk
(74) *Attorney, Agent, or Firm* — Skaar Ulbrich Macari, P.A.

(57) ABSTRACT

A method for anti-inflammatory treatment of diabetic retinopathy can include systemic administration of an A2aAR agonist and providing local electric field stimulation to the retina. The electric field stimulation causes translocation of A2aRs from cytosol to the cell membranes and makes them active and available for binding with adenosine and adenosine agonists. Increased numbers of active A2aRs on cellular membranes leads to several-fold increase in the anti-inflammatory signal transduced into the cells. Amplified adenosine-A2aR signaling pathway causes significant inhibition of production of proinflammatory cytokines and other cytotoxic activity of microglia thus protecting the retina from destruction by the immune system and preserving eyesight. A treatment apparatus can include a multicoil applicator with coils adapted for positioning near eyes for stimulating retina, a pulse generator functionally coupled to the applicator and a power supply.

20 Claims, 5 Drawing Sheets

(51) Int. Cl.
    *A61N 1/32*     (2006.01)
    *A61B 18/00*     (2006.01)

(56) References Cited

U.S. PATENT DOCUMENTS

| | | |
|---|---|---|
| 9,884,199 B2 | 2/2018 | Chornenky et al. |
| 11,129,999 B2 | 9/2021 | Chornenky et al. |
| 2003/0056281 A1* | 3/2003 | Hasegawa ............... A61N 2/002 2/206 |
| 2007/0073096 A1* | 3/2007 | Alvarado ............... G02C 5/001 351/159.01 |
| 2014/0213843 A1* | 7/2014 | Pilla .................. A61N 1/36025 600/14 |
| 2015/0238357 A1* | 8/2015 | Goldberg ............. A61F 9/0008 600/431 |

\* cited by examiner

METHOD AND APPARATUS FOR TREATMENT OF DIABETIC RETINOPATHY (DR)

PRIORITY

This application claims the priority benefit of U.S. Provisional Application No. 62/761,542, filed on Mar. 29, 2018, which is hereby incorporated herein by reference in its entirety.

FIELD

The invention relates to a method and apparatus for anti-inflammatory treatment of diabetic retinopathy. More particularly, the invention relates to an apparatus for producing a pulsed electromagnetic field that provides electric field stimulation of the retina, and to a method for treatment of diabetic retinopathy comprising a combination of systemic administration of an A2aR agonist and application of local pulsed electric field stimulation to the retina.

BACKGROUND

Diabetic retinopathy (DR), one of the most devastating complications of diabetes, is a medical condition in which damage occurs to the retina. Diabetic retinopathy affects up to 80 percent of working age people who have had diabetes for 20 years or more. It is believed that at least 90% of new cases could be prevented if there were a proper treatment. But so far there is none and DR remains the leading cause of blindness in the U.S. and other developed countries.

Recently it has been recognized that the neurodegenerative and inflammatory environment that is prevalent in the diabetic eye is a key player in the development of DR and DR has been categorized as a vascular-neuro inflammatory disease induced by diabetes. Early features of DR include signs of retinal inflammatory reactions, breakdown of the blood-retinal barrier (BRB) and loss of retinal neurons. Under these conditions, normally quiescent microglial cells become activated.

Microglial cells are the residential macrophages of the central nervous system (CNS). They survey the retinal parenchyma and are highly sensitive to alterations in the homeostatic environment of the CNS. Microglial cells act as the first and main form of active immune response in the CNS; they release proinflammatory cytokines, such as TNF-α, IL-1β that activate other immune and parenchymal cells in the retina, and chemokines that recruit neutrophils and monocytes from the retinal blood vessels.

Inflammation of the retina manifests itself through upregulation of endothelial adhesion molecules (ICAM-1/VCAM-1), increased production of nitric oxide, prostaglandin E2, as well as increased permeability and leukostasis in microvasculature of the retina. Adhered neutrophils and monocytes produce reactive oxygen species that lead to endothelial cell damage and cause vascular dysfunction exhibited, in part, in leaking blood through the BRB. Under chronic inflammation microglia secrete reactive oxygen species, nitric oxide (NO), that damage neurons, oligodendrocytes, and essential structures of the extracellular matrix of the retina.

In recent studies, selective anti-inflammatory pharmacologic agents have been demonstrated to significantly inhibit development of the early stages of diabetic retinopathy, especially occlusion and degeneration of retinal capillaries. A common feature of a number of these therapies is that they inhibit production of inflammatory mediators. This new insight into the pathogenesis of diabetic retinopathy offers a new approach to management of DR—the anti-inflammatory treatment.

An important advance in anti-inflammatory treatment of DR was the demonstration of the in vivo efficacy of adenosine Ata receptor (A2aR) agonist CGS21680 in reducing retinal inflammation and cell death. This newly discovered effect of CGS21680 is essential for future development of A2aR-based therapy for DR devoid of the invasive side effects associated with the standard therapy, laser photocoagulation. From a pharmacological standpoint, future challenges include the development of compounds with high and selective-binding affinity to A2aRs, finding delivery path of A2aR agonists to retina and pharmacological strategies of safe use of A2aAR agonists in diabetic patients. Ongoing studies are in progress to further elucidate the role of two potent and selective A2aR agonists ATL370 and ATL313 for their anti-inflammatory effects in diabetic retinopathy.

There is significant evidence that the anti-inflammatory signaling pathway Adenosine-A2aR is a critical pathway for attenuating retinal cell death associated with diabetes. Furthermore, the evidence that the A2aR agonists inhibit release proinflammatory cytokines by deactivating microglia and other immune cells represents a novel therapeutic approach to treat ophthalmic complications associated with diabetes. The discovery of therapy for diabetic retinopathy based on the adenosine-A2aR signaling pathway holds significant potential as an effective therapy.

Adenosine has been proposed to modulate a variety of physiological responses. Under stress conditions, the local levels of extracellular adenosine are increased due to the increased need for energy supplied by ATP and the increased degradation of released ATP. By activating A2aRs at the inflamed sites the increased adenosine concentration protects tissues against the inflammation caused by cellular damage. The adenosine-A2aR pathway downregulates the inflammation and functional changes associated with diabetic retinopathy.

To date the anti-inflammatory effect of the adenosine-A2aR pathway in acute retinal inflammation has been firmly established. Moreover, the adenosine-A2aR pathway has been proven to significantly contribute to retinal protection against chronical diabetes-induced retinal inflammation and injury. It was shown that the activation of the adenosine-A2aR pathway plays a protective role in diabetes-induced retinal cell death by enhancing the anti-inflammatory signaling. These findings suggest that A2aR agonists are promising innovative agents in the treatment of diabetic retinopathy.

Therefore, there is a current need to provide effective modalities of anti-inflammatory therapies based on the Adenosine-A2aR signaling pathway.

Adenosine is a purine nucleoside generated by metabolically stressed or inflamed tissues that is recognized as a major endogenous anti-inflammatory regulator. Under normal conditions, adenosine is continuously released from cells as a product of ATP degradation. Adenosine concentration in extracellular space is controlled by an enzyme called adenosine deaminase (ADA) which breaks it down and keeps the concentration level in a low-micromolar to high-nanomolar range. However, during conditions of stress, such as hypoxia during inflammation, levels of extracellular adenosine rise dramatically (up to 200-fold). Adenosine regulates the function of the innate and adaptive immune systems through targeting virtually every cell type that is involved in orchestrating the immune/inflammatory response. Of the four adenosine receptors (A1, A2a, A2b, A3), A2a receptors have taken center stage as the primary anti-inflammatory effectors of extracellular adenosine. This broad, anti-inflammatory effect of A2aRs activation is a result of the predominant expression of A2aRs on all immune cells in the body. A2aRs play a critical role in controlling leukocyte trafficking by suppressing the release of cytokines that induce production of adhesion molecules (ICAM-1/VCAM-1) and promote the "roll", "stop" and "exit" mechanism bringing neutrophils and monocytes from blood vessels into tissues.

A2aR activation inhibits early and late events occurring during an immune response, which include immune cell trafficking, immune cell proliferation, proinflammatory cytokine production, and cytotoxicity. In late stages of inflammation, in addition to limiting inflammation, A2aRs participate in tissue remodeling and restoration. Consistent with their multifaceted, immunoregulatory action on immune cells, A2aRs have been shown to impact the course of a wide spectrum of ischemic, autoimmune, infectious, and allergic diseases.

The protective effect of stimulation of A2aRs was proven to correlate with decreased expression of adhesion molecules (ICAM-1/VCAM-1) and reduction of transmigration of neutrophil and monocytes from blood vessels to surrounding tissues. In addition, the retinal microvasculature responds to A2aRs stimulation by vasodilation that results in increased blood flow in the retinal microcirculation and contributes to the retinal protection.

Pulsed Electromagnetic Field Therapy (PEMF) is a non-invasive method of treatment of numerous medical conditions related to injuries and inflammations of different tissues: bones, cartilages, soft and neurological tissues. For centuries it was common knowledge that natural wound healing involves generation of endogenous electric fields. Recently it has been discovered that the endogenous electric fields also control the processes of remodeling and healing bones and cartilages.

In PEMF therapy, the electric field is carried into the treatment zone by a pulsed magnetic field produced by electromagnetic coils from outside the body. A PEMF system applies a series of magnetic pulses to injured tissue where each magnetic pulse induces an electrical signal that stimulates cellular anti-inflammatory and anabolic activities. PEMF therapy reduces pain associated with inflammation by suppressing production of pain mediator prostaglandin E2 and accelerates natural healing of tissues. Multiple studies have demonstrated effectiveness and safety of PEMF therapy in suppressing inflammation.

Recently it has been established by Varani et al. that the anti-inflammatory mechanism action of PEMF on a cell is due to its ability to increase the concentration of A2aRs on the cell membrane. PEMF stimulation increases the number of active A2aRs by translocating them from cytoplasm on the cell membrane and making them active and available for binding with adenosine ligand. Generally, the signal to a cell and the biological response of the cell's machinery depends on both the concentration of ligands in the extracellular space and the concentration of receptors on the cell membrane. As a result, the same cellular response can be achieved by two different ways: by changing concentration of adenosine or adenosine like drugs around the cell or by changing concentration of the receptors on the cell membrane. The essence of discovery of Varani et al. is that the adenosine signaling pathway can be up-regulated without increasing extracellular adenosine concentration. It can be achieved by increasing concentration of A2aRs on the cellular membranes by applying electric field stimulation alone.

Thus, there is a continuing need to develop efficient diabetic retinopathy treatments using PEMF.

SUMMARY

An objective herein is to provide a method for treatment of diabetic retinopathy by activating the Adenosine-A2aR anti-inflammatory pathway. Another objective herein is to provide an apparatus for treatment of diabetic retinopathy by activating the Adenosine-A2aR anti-inflammatory pathway. These objectives are achieved by providing a method of administration of an A2aR agonist systemically and by providing a PEMF system delivering electrical stimulation to the retina of a diabetic eye that increases the number of active A2aRs on the cellular membranes and downregulates inflammation by amplifying the adenosine-A2aR anti-inflammatory pathway.

Another objective is to provide a portable PEMF system for treatment of diabetic retinopathy that can be used by a user during everyday activity. The objective is achieved by providing a PEMF system secured on a frame that is similar or comparable to a frame of glasses and can be worn permanently.

Yet another objective is to provide a stationary PEMF system for office or home with a relatively high stimulating electric field and increased overall effectiveness of treatment of diabetic retinopathy. The objective is achieved by providing such a PEMF system as disclosed herein.

Provided herein is a pulsed electro-magnetic field (PEMF) stimulation apparatus for treatment of diabetic retinopathy (DR). The apparatus can comprise a frame configured to rest on a nose bridge of a user, a first coil provided to the frame and positioned adjacent to a first eye of the user, a second coil provided to the frame and positioned adjacent to a second eye of the user, and a controller coupled to each of the first coil and the second coil and configured to periodically switch directions of an electric current in the first coil and the second coil during a treatment regimen.

The first and second coils each can be disposed in front of the eyes of the user or can be disposed beside a respective temple area of the user.

A third coil can be provided to the frame and positioned adjacent to the first eye of the user in a different plane than the first coil. A fourth coil can be provided to the frame and positioned adjacent to the second eye of the user in a different plane than the second coil. The third coil and the fourth coil are coupled to the controller.

The first and second coils can each be disposed in front of the eyes of the user with the third and fourth coils each disposed along side a respective temple area of the user. The controller is configured to alternate pulses between the first and third coils, and alternate pulses between the second and fourth coils.

The frame is configured as a pair of eyeglasses or as a pair of safety goggles. A flexible arc clip can be configured to secure the frame to the head of the patient Also provided is a method of treating DR in a patient. The method can include providing PEMF stimulation to a patient's eye cells to cause electrically sensitive adenosine A2aR receptors in the patient's eye cells to translocate to a cellular membrane surface, where the electrically sensitive adenosine A2aR receptors bind with free adenosine or adenosine-like drugs from an intercellular space to activate an adenosine-A2aR anti-inflammatory signaling pathway in the patient's eyes.

The method can further include delivering PEMF stimulation to the patient's eyes via a first coil disposed in front of a first eye of the patient and a second coil disposed in front of a second eye of the patient. The method can further include delivering the PEMF stimulation to the patient's eyes via a third coil disposed to a side of the first eye of the patient and a fourth coil disposed to a side of the second eye of the patient. Pulses can be alternated between the first and third coils and between the second and fourth coils.

The method can include delivering the PEMF stimulation to the patient's eyes via a first coil disposed to a side of a first eye of the patient and a second coil disposed to a side of a second eye of the patient.

A treatment applicator can be disposed about a head of the patient. The treatment applicator can be an eyeglass frame, a pair of goggles or other fixture to support the applicator about the head of the patient.

Further provided is a PEMF stimulation apparatus for treatment of DR. The apparatus can include a chair, a head support provided to the chair, a first adjustable mount provided to the head support, a second adjustable mount provided to the heard support, a first PEMF applicator disposed at a distal end of the first adjustable mount, and a second PEMF applicator disposed at a distal end of the second adjustable mount.

The first PEMF applicator can comprise a plurality of coils and the second PEMF applicator comprises a plurality of coils, wherein each of the coils in each applicator are arranged to provide electrical stimulation to a patient's eyes in at least three orthogonal directions when the patient is seated in the chair.

A controller can be configured to deliver PEMF stimulation to a patient's eyes via a first coil provided to the first PEMF applicator and a second coil provided to the second PEMF applicator. The controller can be configured to provide PEMF stimulation to a patient's eye cells to cause electrically sensitive adenosine A2aR receptors in the patient's eye cells to translocate to a cellular membrane surface, where the electrically sensitive adenosine A2aR receptors bind with free adenosine or adenosine-like drugs from an intercellular space to activate an adenosine-A2aR anti-inflammatory signaling pathway in the patient's eyes.

The detailed technology and preferred embodiments implemented for the subject invention are described in the following paragraphs accompanying the appended drawings for people skilled in this field to well appreciate the features of the claimed invention. It is understood that the features mentioned hereinbefore and those to be commented on hereinafter may be used not only in the specified combinations, but also in other combinations or in isolation, without departing from the scope of the present invention.

Figure 1:
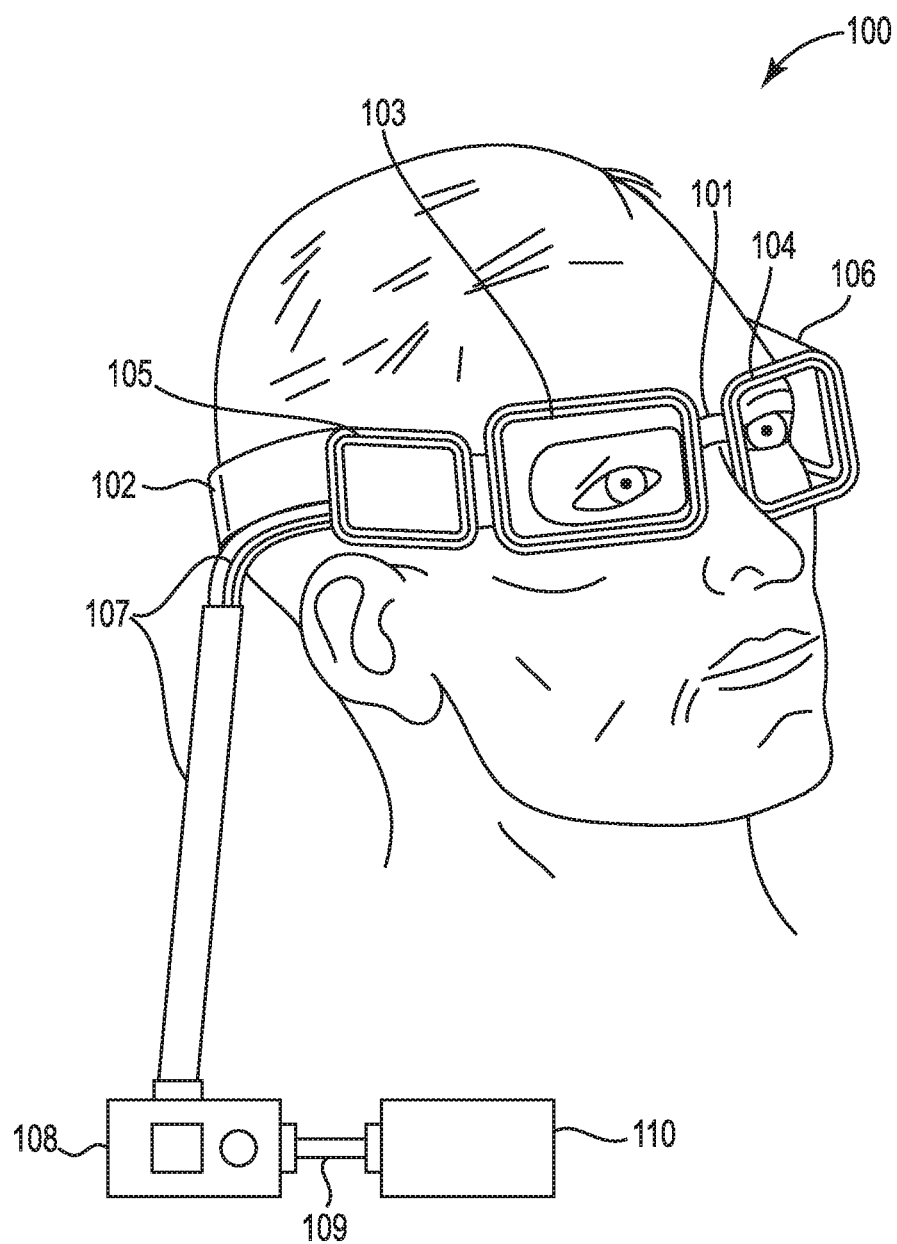
FIG. 1 depicts an apparatus for treatment of diabetic retinopathy shown as being worn by a patient according to certain embodiments.

While the invention is amenable to various modifications and alternative forms, specifics thereof have been shown by way of example in the drawings and will be described in detail. It should be understood, however, that the intention is not to limit the invention to the particular example embodiments described. On the contrary, the invention is to cover all modifications, equivalents, and alternatives falling within the scope of the invention as defined by the appended claims.

DETAILED DESCRIPTION

In the following descriptions, the present invention will be explained with reference to various example embodiments; nevertheless, these example embodiments are not intended to limit the present invention to any specific example, embodiment, environment, application, or particular implementation described herein. Therefore, descriptions of these example embodiments are only provided for purpose of illustration rather than to limit the present invention.

Diabetic retinopathy progresses through four stages: mild nonproliferative retinopathy, moderate nonproliferative retinopathy, severe nonproliferative retinopathy and proliferative diabetic retinopathy (PDR). The method of treatment of DR provided herein can be effective in all three nonproliferative stages of the disease, and the earlier stage the better.

An apparatus for treatment of diabetic retinopathy 100 is shown in FIG. 1. A glasses-like frame 101 formed of insulating material rests on the nose bridge of a patient and is secured on his head with a belt or strap 102. Numerals 103 and 104 designate the electromagnetic coils positioned at the front side of the right and left eyes correspondingly. Further electromagnetic coils 105 and 106 are secured at the right and the left sides of the glasses-like frame 101. A multi-conductor cable 107 functionally connects all four coils 103, 104, 105 and 106 with a computerized controller 108 that provides to each coil electrical pulses with predetermined sequence, amplitude, polarity, and repetition rate. Power cable 109 connects controller 108 with a battery or another power source 110.

Controller 108 generates rectangular (DC) pulses that are applied in predetermined sequence to the coils 103, 104, 105 and 106, creating changing magnetic fields inside of the coils. The duration of the pulses is required to be more than the time of electrical relaxation of a biological cell, which is about 1 microsecond. Practically employed durations can be in the range of 10 to 1000 microseconds. The time of relaxation of the coil $\tau=L/R$, where L is inductance of the coil and R is it's resistance, is selected to be at least several times higher than the duration of the pulses, which leads to close to linear growth of the current and magnetic field and makes corresponding electrical field pulses generated by the changing magnetic fields approximately rectangular.

The electrical field pulses applied to the retina via the coils cause the electrically sensitive adenosine A2aR receptors to translocate to the surface of the cellular membranes, where they bind with free adenosine or adenosine like drugs from the intercellular space. This process activates in parenchymal and macroglial cells of the retina the adenosine-A2aR anti-inflammatory signaling pathway which is the major objective of the present invention.

In another implementation of the invention, only the two coils 103 and 104 in front of the eye can be used, without side coils 105 and 106, or vice versa, with only the side coils 105 and 106 without the front coils 103, 104.

Also, side coils 105 and 106 can be configured as attachable and removable "clips" that can be used with standard vision glasses.

Figure 2:
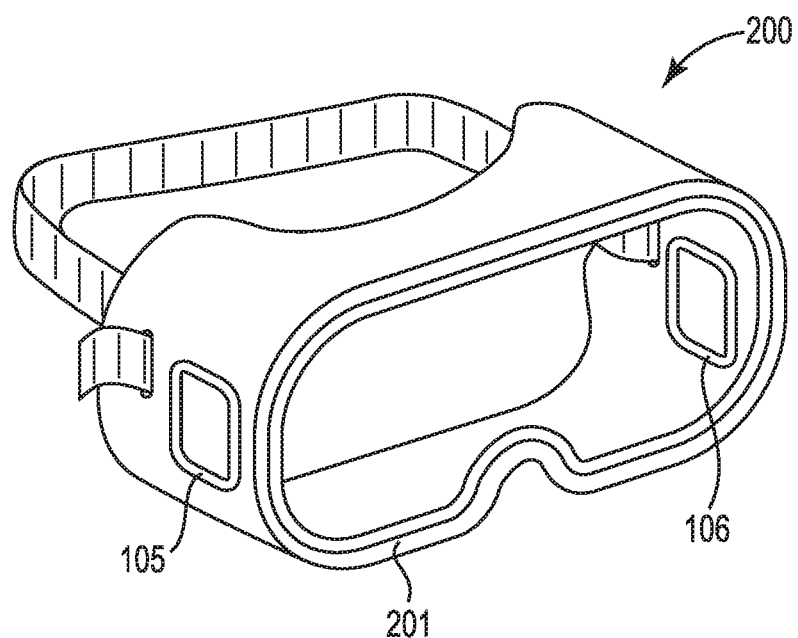
FIG. 2 is a perspective view of an apparatus for treatment of diabetic retinopathy with a goggles-like frame according to certain embodiments.

In FIG. 2 another implementation of the treatment apparatus 200 is shown. Here the PEMF stimulating coils 105, 106 are secured on a protecting goggles-like frame which can be put over the patient's standard glasses while wearing the glasses. In this implementation the side coils 105 and 106 are located proximately to the eyes exactly as in FIG. 1, but instead of two front coils 103 and 104 only one front coil 201 is provided.

Figure 3:
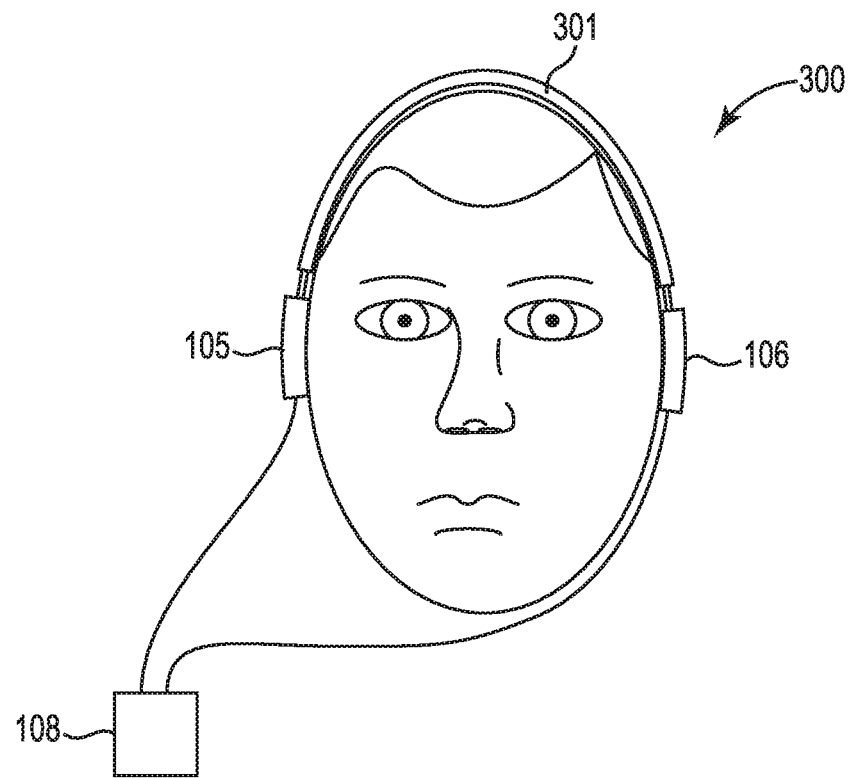
FIG. 3 is a view of a treatment apparatus with an over-the-head clip on the head of a patient according to certain embodiments.

FIG. 3 illustrates another embodiment of the treatment apparatus 300 where the side coils 105 and 106 are held in close proximity to the patient's eyes by a flexible arc clip 301 which secures the coils to the head of the patient. This PEMF system 300 also can be used simultaneously with standard glasses.

Figure 4:
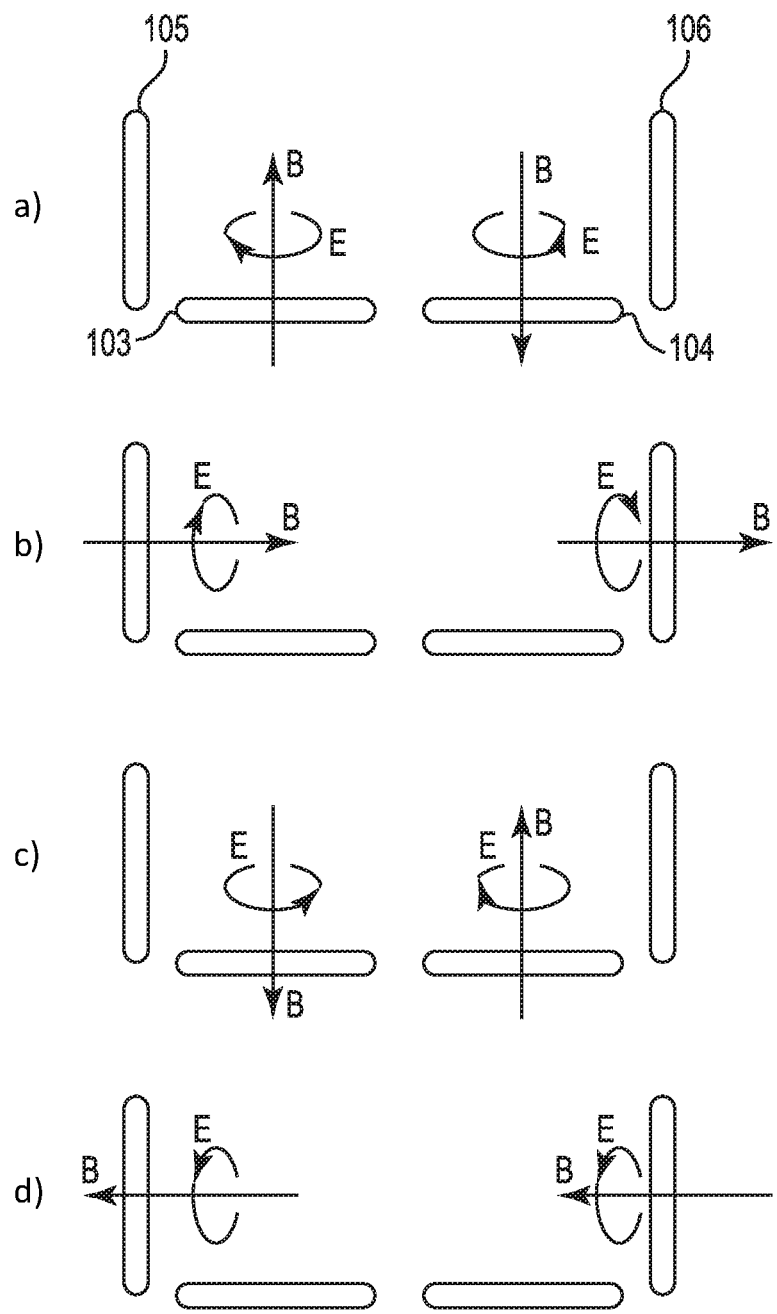
FIG. 4 is a series of four schematics depicting the spatial patterns of pulsed magnetic and electric fields during PEMF stimulation of a diabetic patient's eyes according to certain embodiments.

In the embodiment of FIG. 1, the sequence of pulses delivered by the controller to the coils 103, 104, 105 and 106 is exemplary illustrated by sequence a), b), c), d) in FIG. 4. Cycles a) and b) are activated consecutively in sequence "front-side-front-side" etc. It should be mentioned that different pulse sequences can be selected, as well as the durations of each cycle with a given mode of pulsing. Straight arrows show the direction of magnetic field B in each coil and circular arrows show the direction of the electrical field E induced in the retina.

In an exemplary implementation of the invention the duration of cycles a) and b) may last around 10-15 minutes with switching every 10-15 minutes to opposite polarity of magnetic and electric fields in cycles c) and d), up to 30-40 minutes per session. The 10-15 minute pauses between applying electrical field pulses of different polarities leave newly activated A2aRs undisturbed about 10-15 minutes which allows them to bind with adenosine and contribute to activation of the adenosine-A2aR anti-inflammatory pathway.

Two-dimensional PEMF stimulation is employed with opposite polarities of pulsing to allow increasing the number of A2aRs on the cells available for binding by a factor of 3-4 times as compared to the base number. As was demonstrated by Katia Varani et al., the downstream anti-inflammatory action of adenosine-A2aR pathway increases as the square of the number of the receptors. This means that the 3-4 increase in number of activated receptors increases anti-inflammatory action by 9-16 times. The same anti-inflammatory action cannot be achieved pharmaceutically by increasing concentration of adenosine 9-16 times because of side effects of the drugs employed for controlling the anti-inflammatory response. The efficient level of anti-inflammatory treatment was demonstrated to be 4-5 times that of the base level.

Figure 5:
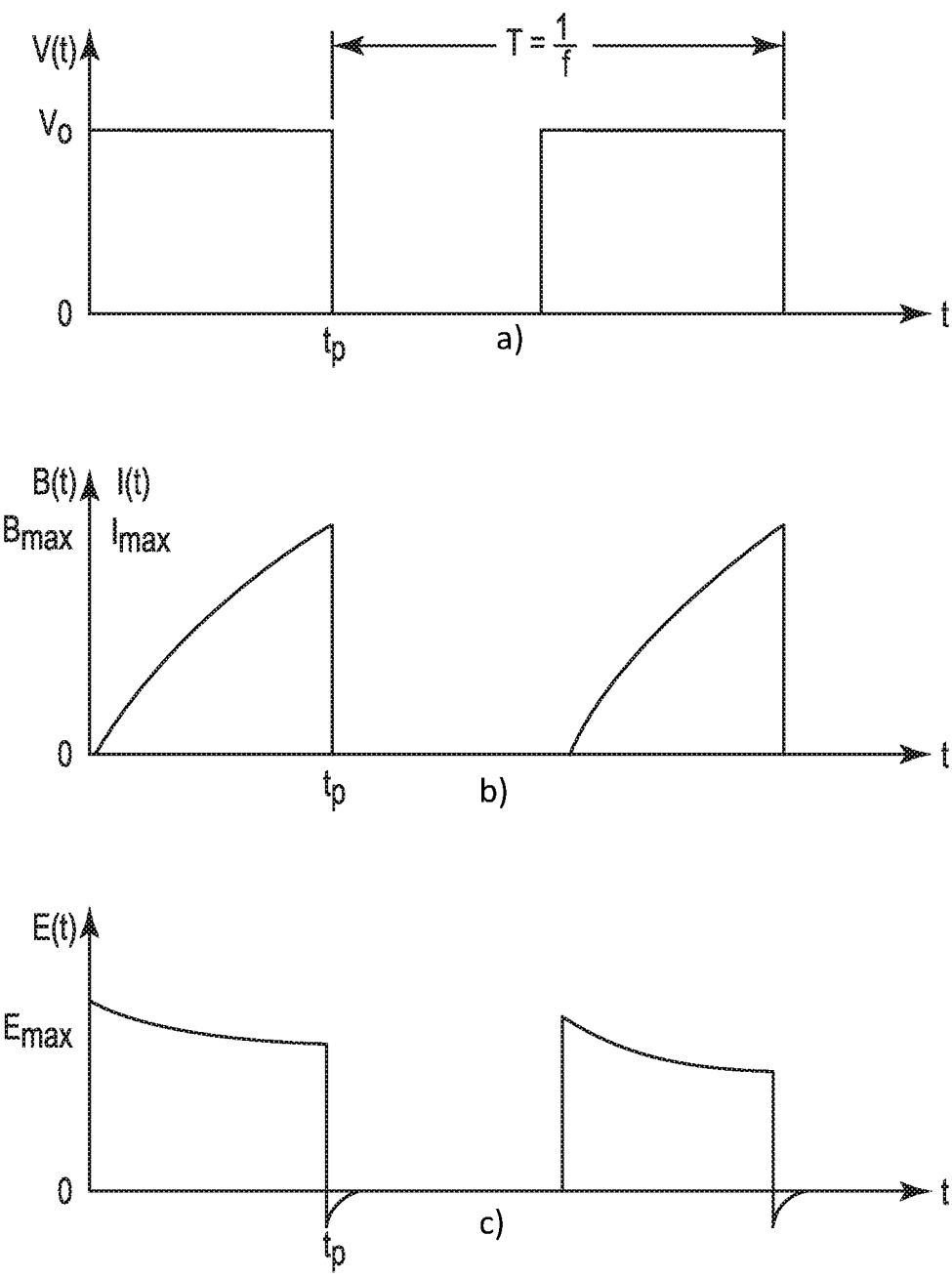
FIG. 5 is a series of diagrams of wave forms of pulses generated by a controller during stimulation of a patient's diabetic eyes according to certain embodiments.

FIG. 5 illustrates waveforms of the pulses generated on the coils 103, 104, 105 and 106 and in the treatment zone. FIG. 5 at (a) is a diagram of voltage V(t) applied to the coils; (b) depicts the electric current I(t) through coils and magnetic field B(t) at the treatment zone; and (c) depicts the electric field E(t) in the treatment zone. The duration of the pulses $t_p$ lies in the range from 10 to 1000 microseconds. The period T between sequential pulses is in the 10 to 200 millisecond range, which corresponds to frequency (repetition rate) range f=5-100 Hertz. FIG. 5 depicts only positive polarity of the pulses. The negative polarity pulses could also be used in the PEMF system.

Figure 6:
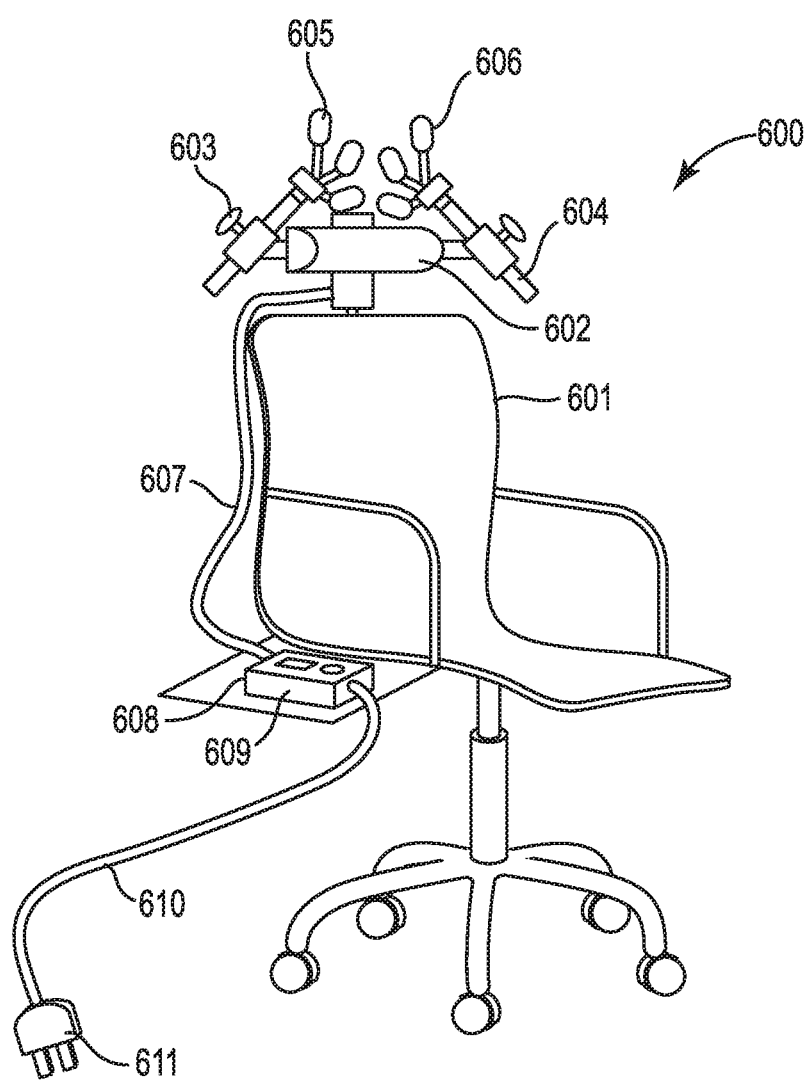
FIG. 6 is a perspective view of a treatment apparatus suitable for office or home use according to certain embodiments.

In FIG. 6 another implementation of the treatment apparatus 600 is schematically depicted. This version of the apparatus is not portable but rather stationarily secured on a therapeutic chair 601. Chair 601 has a head support 602 on which adjustable mounts 603 and 604 are attached. At the ends of mounts 603 and 604 applicators 605 and 606 are secured. Each applicator 605, 606 includes preferably three coils that during a treatment session are positioned in close proximity to the patient's eyes while sitting in the chair. The spatial positions of the coils to each other are selected in such a manner that they provide electrical stimulation of the patient's eyes in three orthogonal directions, thus providing maximum possible effect of stimulation. Multi wire cable 607 connects applicators 605 and 606 with computerized controller 608 attached to a shelf 609 secured to chair 601. Power cable 610 is connected to a connector 611.

It is also within the scope of the invention to combine features, functions, advantages and aspects of the various embodiments described herein. Thus, the embodiments of the invention may comprise combinations of aspects of any one or more of these exemplary embodiments.

While the invention has been described in connection with what is presently considered to be the most practical and preferred example embodiments, it will be apparent to those of ordinary skill in the art that the invention is not to be limited to the disclosed example embodiments. It will be readily apparent to those of ordinary skill in the art that many modifications and equivalent arrangements can be made thereof without departing from the spirit and scope of the present disclosure, such scope to be accorded the broadest interpretation of the appended claims so as to encompass all equivalent structures and products.

For purposes of interpreting the claims for the present invention, it is expressly intended that the provisions of Section 112, sixth paragraph of 35 U.S.C. are not to be invoked unless the specific terms "means for" or "step for" are recited in a claim.

What is claimed is:

1. A pulsed electro-magnetic field (PEMF) stimulation apparatus for treatment of diabetic retinopathy (DR), the apparatus comprising:
   a frame;
   a first coil provided to the frame and positioned adjacent to a first eye of the user;
   a second coil provided to the frame and positioned adjacent to a second eye of the user; and
   a controller coupled to each of the first coil and the second coil and configured to periodically switch directions of an electric current in the first coil and the second coil during a treatment regimen.

2. The apparatus of claim 1, wherein the first and second coils are each disposed in front of the eyes of the user.

3. The apparatus of claim 1, wherein the first and second coils are each disposed beside a respective temple area of the user.

4. The apparatus of claim 1, wherein the frame is configured as a pair of eyeglasses.

5. The apparatus of claim 1, wherein the frame is configured as a pair of safety goggles.

6. The apparatus of claim 1, wherein the frame is configured as a flexible arc clip configured to secure the frame to the head of the patient.

7. The apparatus of claim 1, wherein the frame is configured to rest on a nose bridge of a user.

8. A pulsed electro-magnetic field (PEMF) stimulation apparatus for treatment of diabetic retinopathy (DR), the apparatus comprising:
- a frame;
- a first coil provided to the frame and positioned adjacent to a first eye of the user;
- a second coil provided to the frame and positioned adjacent to a second eye of the user;
- a third coil provided to the frame and positioned adjacent to the first eye of the user in a different plane than the first coil; and
- a fourth coil provided to the frame and positioned adjacent to the second eye of the user in a different plane than the second coil, and
- a controller coupled to each of the first coil, the second coil, the third coil and the fourth coil, and configured to periodically switch directions of an electric current in the first coil and the second coil during a treatment regimen.

9. The apparatus of claim 8, wherein the first and second coils are each disposed in front of the eyes of the user, and wherein the third and fourth coils are each disposed along side a respective temple area of the user.

10. The apparatus of claim 8, wherein the controller is configured to alternate pulses between the first and third coils, and alternate pulses between the second and fourth coils.

11. The apparatus of claim 8, wherein the first and second coils are each disposed in front of the eyes of the user.

12. The apparatus of claim 8, wherein the first and second coils are each disposed beside a respective temple area of the user.

13. The apparatus of claim 8, wherein the frame is configured as a pair of eyeglasses, a pair of safety goggles, or as a flexible arc clip configured to secure the frame to the head of the patient.

14. The apparatus of claim 8, wherein the frame is configured to rest on a nose bridge of a user.

15. A pulsed electro-magnetic field (PEMF) stimulation apparatus for treatment of diabetic retinopathy (DR), the apparatus comprising:
- a frame;
- a first coil provided to the frame and positioned adjacent to a first eye of the user;
- a second coil provided to the frame and positioned adjacent to a second eye of the user;
- a third coil provided to the frame and positioned adjacent to the first eye of the user in a different plane than the first coil; and
- a fourth coil provided to the frame and positioned adjacent to the second eye of the user in a different plane than the second coil, and
- a controller coupled to each of the first coil, the second coil, the third coil and the fourth coil, and configured to alternate pulses between the first and third coils, and alternate pulses between the second and fourth coils, during a treatment regimen.

16. The apparatus of claim 15, wherein the first and second coils are each disposed in front of the eyes of the user, and wherein the third and fourth coils are each disposed along side a respective temple area of the user.

17. The apparatus of claim 15, wherein the first and second coils are each disposed in front of the eyes of the user.

18. The apparatus of claim 15, wherein the first and second coils are each disposed beside a respective temple area of the user.

19. The apparatus of claim 15, wherein the frame is configured as a pair of eyeglasses, a pair of safety goggles, or as a flexible arc clip configured to secure the frame to the head of the patient.

20. The apparatus of claim 15, wherein the frame is configured to rest on a nose bridge of a user.

* * * * *